Figure 1:
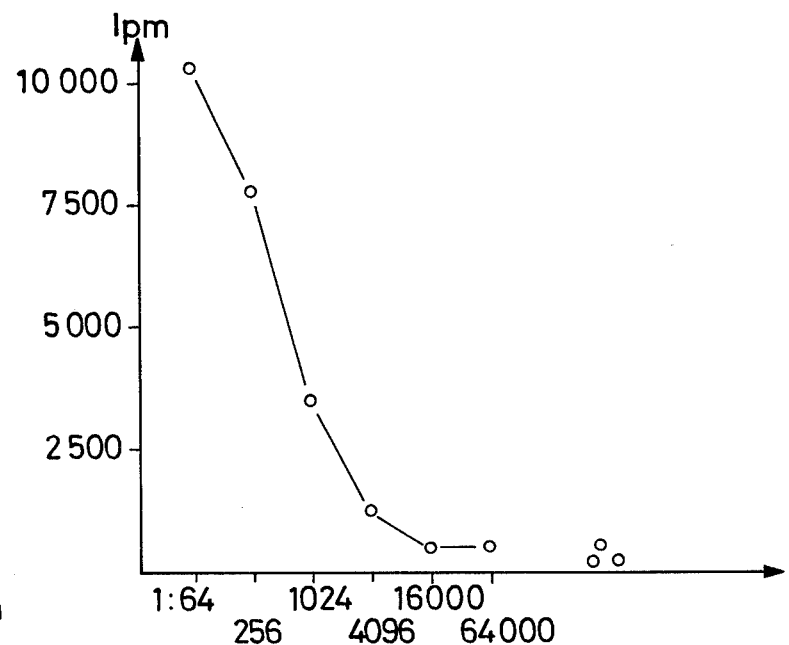

United States Patent [19]

Schober

[11] 4,172,117
[45] Oct. 23, 1979

[54] METHOD FOR THE SIMULTANEOUS MEASUREMENT OF ANTIGENS AND THEIR ANTIBODIES BY SOLID-PHASE RADIOIMMUNOASSAY

[75] Inventor: Andreas Schober, Göttingen, Fed. Rep. of Germany

[73] Assignee: Biotest-Serum-Institut GmbH, Frankfurt/M.—Niederrad Fed. Rep. of Germany

[21] Appl. No.: 838,332

[22] Filed: Sep. 30, 1977

Related U.S. Application Data

[63] Continuation of Ser. No. 578,838, May 19, 1975, abandoned.

[30] Foreign Application Priority Data

May 20, 1974 [DE] Fed. Rep. of Germany ....... 2424465

[51] Int. Cl.$^2$ ..................... G01N 23/00; G01N 33/16; G01T 1/16
[52] U.S. Cl. ...................................... 424/1; 23/230 B; 23/230.6; 250/303; 424/12
[58] Field of Search ................... 23/230, 230 B, 230.3, 23/230.6; 424/1, 1.5, 12

[56] References Cited

U.S. PATENT DOCUMENTS

| | | | |
|---|---|---|---|
| 3,646,346 | 2/1972 | Catt | 23/230 B X |
| 3,733,398 | 5/1973 | Shulman | 424/12 |
| 3,826,619 | 7/1974 | Bratu, Jr. | 23/230 B X |
| 3,867,517 | 2/1975 | Ling | 23/230 B X |
| 3,872,225 | 3/1975 | Coller | 23/230 B X |
| 3,904,367 | 9/1975 | Golibersuch | 23/253 TP X |
| 3,949,064 | 4/1976 | Bornstein | 424/1 |

OTHER PUBLICATIONS

Clin. Chem., v. 19, pp. 146 and 161–163 (1973).

*Primary Examiner*—Sidney Marantz
*Attorney, Agent, or Firm*—Sprung, Felfe, Horn, Lynch & Kramer

[57] ABSTRACT

Antigens and their antibodies are measured in a combined radioimmunoassay by incubating a sample of an unknown fluid with a known quantity of an antibody, contacting the mixture obtained with the walls of a vessel having a coating of known antigen content, again incubating, then aspirating the mixture and washing the walls of the vessel, adding a pure radioactive tracer antigen, aspirating and washing again, and finally measuring the radioactivty of the coated parts conventionally, e.g., in a gamma counter known in the art.

10 Claims, 4 Drawing Figures

| ASSAY PERFORMANCE | NEGATIVE CONTROLS: AG NEGATIVE AND AB NEGATIVE | AG POSITIVE SERUM AG: △ | AB POSITIVE SERUM AB: X |
|---|---|---|---|
| 1. IN EMPTY MICRO-TITRATION PLATE: SAMPLE OF SERUM + STANDARD AB SERUM; INCUBATION; |  |  |  |
| 2. SAMPLE FROM IST INCUBATION MIXTURE IN AG-COATED MICRO-TITRATION PLATE; INCUBATION; ASPIRATION & WASHING |  |  |  |
| 3. ADDITION OF $^{125}$I TRACER AG: △ ; INCUBATION; ASPIRATION & WASHING |  |  | |
| 4. MEASUREMENT OF THE RADIOACTIVITY; RATIO OF THE COUNT RATES | 4 | 2 | 6 |

AG = ANTIGEN, AB = ANTIBODY, ▽$^x$ = RADIOACTIVE ANTIGEN

FIG. 4.

| ASSAY PERFORMANCE | NEGATIVE CONTROLS: Ag NEGATIVE AND Ab NEGATIVE | Ag POSITIVE SERUM Ag: △ | Ab POSITIVE SERUM Ab: Y |
|---|---|---|---|
| 1. IN EMPTY MICRO-TITRATION PLATE: SAMPLE OF SERUM + STANDARD Ab SERUM; INCUBATION; | XXXX | XXXX | XXXX XX |
| 2. SAMPLE FROM 1ST INCUBATION MIXTURE IN Ag-COATED MICRO-TITRATION PLATE; INCUBATION; ASPIRATION & WASHING | | | |
| 3. ADDITION OF $^{125}I$ TRACER Ag: △; INCUBATION; ASPIRATION & WASHING | | | |
| 4. MEASUREMENT OF THE RADIOACTIVITY; RATIO OF THE COUNT RATES | 4 | 2 | 6 |

Ag = ANTIGEN, Ab = ANTIBODY, ▽$^x$ = RADIOACTIVE ANTIGEN

METHOD FOR THE SIMULTANEOUS MEASUREMENT OF ANTIGENS AND THEIR ANTIBODIES BY SOLID-PHASE RADIOIMMUNOASSAY

This is a continuation of application Ser. No. 578,838, filed May 19, 1975, now abandoned.

The invention relates to a method for the simultaneous measurement of antigens and their antibodies through solid-phase radioimmunoassay.

It is known that antigens or their antibodies can be detected in an unknown sample through direct or indirect radioimmunotesting (see, for instance Catt, K. and Tregear, C. W., Science 158 (1967) pp. 1570–1572 "Solid-Phase Radioimmunoassay in Antibody-Coated Tubes"). It has not been possible, however, to measure antigens or their antibodies radioimmunologically in a single assay procedure. Surprisingly, according to the invention, it is possible to measure antigens and their antibodies in a relatively short and simple method using a combined radioimmunoassay.

The invention provides a method for the simultaneous measurement of antigens having at least one binding site, or their antibodies having at least two binding site.

Essentially the invention comprises incubating a sample of an unknown serum with a known quantity of antibody and contacting the mixture obtained with the walls of a vessel having a coating of known antigen content, again incubating, then aspirating the mixture and washing the walls of the vessel adding a pure radioactive tracer antigen, aspirating and washing again, and finally measuring the radioactivity of the coated parts conventionally, e.g., in a gamma counter known in the art.

The so-called "unkown" serum to be tested may be a non-coagulating whole blood, plasma, serum or any other body fluid, such as urine or saliva.

For the first incubation phase, it is preferable to use 10 to 15% of the quantity of antibody maximally bondable by the coating of the reaction vessel to be employed. Micro-titration plates, assay tubes or other appropriate devices can be used as reaction vessels. The incubation is performed for 1 to 16 hours within a temperature range of 20° to 50° C., preferably 1 hour a 37° C. or 12 hours at 20° C. Longer incubation times may be used.

Antigens and antibodies which can be measured according to the method in accordance with the invention are for example viruses or virus subunits such as hepatitis-B antigens or hepatitis-B antibodies and the Coxsackie viruses A and $B_5$ bacteria, membranes, cell membranes, various hormones, for example insulin, drugs such as antibiotics, gamma globulins and the like.

The liquids to be used for washing or rinsing should preferably be of neutral pH.

As a close relationship of $HB_s$ antigen with hepatitis-B has been proven to exist, and, since $HB_s$ antigen positive blood can carry the agent of hepatitis-$B_s$ which leads to a clinically determinable or also a clinically nondeterminable infection in the recipient in so far as he is not immune, it is of great importance to determine whether $HB_s$ antigen is present in the blood of donors. $HB_s$ antibody has clinical importance in that it can be detected in a high percentage in the convalescence phase of a hepatitis-B infection. It is further not yet known whether preserved blood, the serum of which contains $HB_s$ antibody, can also carry the agent of hepatitis-B. Therefore, as sensitive a measurement as possible of HB antibody is an important concern in hospitals.

The method of the invention is exemplified, without limitation, below in an embodiment to measure HB antigen and antibody.

EXAMPLE 1

Direct Radioimmunoassay on $HB_s$ Antibody

Micro-titration plates that can be cut up, for instance those made by the Cooke company, are coated with a mixture of purified $HB_s$ antigen of both subtypes D and Y (Schober, A., R. Thomssen, and U. Kaboth, "Deutsche Medizinische Wochenschrift" (German Medical Weekly) 97 (1972), pp. 1579–1583 "Serologische Subtypen des Hepatitis-B-Antigen (Australia-Antigen)". The mixture is alkaline (0.01 N-tris-buffer, pH 9.5) and contains about 300 ng $HB_s$ antigen protein per ml.

The purification of $HB_s$ antigen from whole serum was performed according to the so-called Ro-S-procedure (Ro=density, S=sedimentation), i.e. a combined density equilibrium and sedimentation gradient centrifugation, performed in cesium chloride. Criteria of the purity of the preparations are their deficient reaction with human antiserum in the immunodiffusion test as well as the lack of reaction of antibodies, produced with these preparations in the experimental animal, with human serum proteins.

$HB_s$ antigen used for coating is maintained for at least 5 hours at 20° C. in the wells of the micro-titration plates, then aspirated. After rinsing five times with a neutral buffer solution (0.01 M-tris-buffer, pH 7.5), samples of a dilution of a standard HB antiserum containing as much as possible only the specific subtype determinant anti-a, are introduced with a pipette. After an incubation of for instance 1 hour at 37° C. or 12 hours at 20° C., the contents are again aspirated and the plate rinsed. Next 125 I tracer HB antigen (produced according to W. M. Hunter and F. C. Greenwood, Nature 194 (1962) p. 495), also a mixute of both subtypes that renders between 20,000 and 40,000 impulses per minute (IpM) 0.1 ml, is added and incubated for 1 hour at 37° C. or 12 hours at 20° C. After further aspiration and rinsing, the micro-titration plates are cut up and the radioactivity is measured in a gamma counter. With low serum dilutions of standard HB antibody, a high pulse count is obtained which diminishes in the further diluted samples and finally reaches the impulse value of the negative controls carried along simultaneously as illustrated in FIG. 1, which is a plot of pulse counts against dilution ratios;

The specificity of this direct $HB_s$ antibody assay was confirmed by inhibition tests. A determined quantity of $HB_s$ antigen is thereby added to the material to be tested on $HB_s$ antibody and incubated, for instance, for 1 hour at 37° C. using tubes or micro-titration plates which have not been coated with $HB_s$ antigen. After this incubation the mixture is incubated in $HB_s$-antigen-coated plates, followed by aspiration and washing. Thereupon 125 I tracer $HB_s$ antigen is added and a further incubation is performed. After aspiration and washing the radioactivity is measured. If HB antibodies are present in the material to be tested, these antibodies will be removed by the added antigen and consequently cannot be bound anymore to the antigen present on the solid surface during the second incubation. (Hence the designation "inhibition test").

Antiglobulin or anti-B-lipo-proteins possibly present in the test serum do not lead to incorrect positive results. Tests have shown that all impulse values obtained are to be considered as specific for $HB_s$ antibodies which are reproducibly over 2.0 times the mean value of the negative controls, as shown in the following table.

TABLE 1

Relationship between specificity and mean value $\overline{X}$ of the negative controls.

| Factor | number of serum samples | specific | % |
|---|---|---|---|
| $\leq \overline{X}$ | 183 | 0 | 0 |
| $\overline{X}$-1.5 $\overline{X}$ | 169 | 0 | 0 |
| 1.5 $\overline{X}$-2 $\overline{X}$ | 17 | 6 | 33 |
| 2 $\overline{X}$-2.5 $\overline{X}$ | 5 | 5 | 100 |
| >2.5 $\overline{X}$ | 48 | 48 | 100 |
|  | 422 |  |  |

EXAMPLE 2

Figure 3:
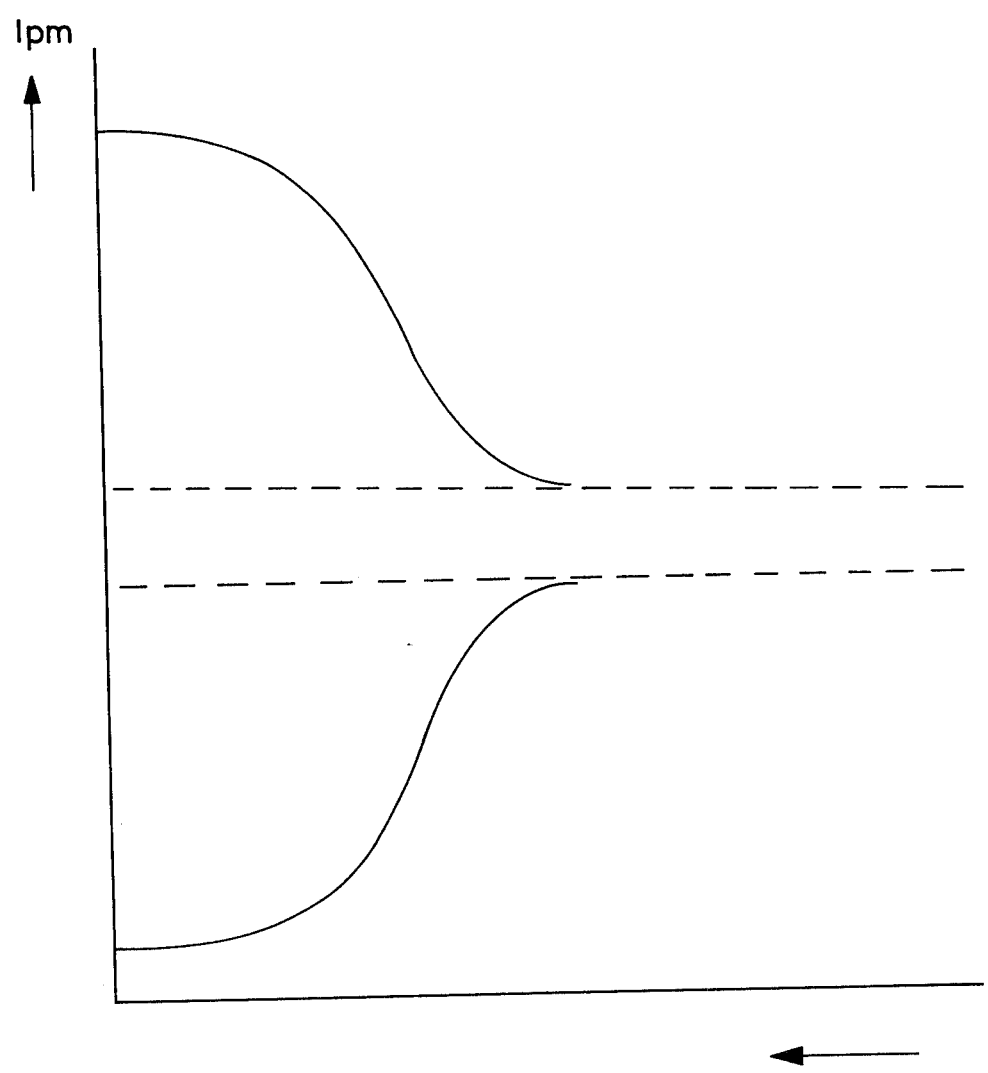

The assay described in Example 1 is suitable for combined $HB_s$ antigen and antibody measurement if a preliminary incubation of the serum to be tested is performed wth a relatively low quantity of $HB_s$ antibody given in advance. If the test serum contains $HB_s$ antigen, an impulse reduction in relation to the negative controls is observed in the solid-phase radioimmunoassay performed according to Example 1, whereas an impulse increase can be determined if sufficient quantities of $HB_s$ antibodies are present, since the count is further added to the antibody given in advance as shown in FIG. 3, which is a plot of pulse counts against the quantity of antigen and antibody.

Figure 2:
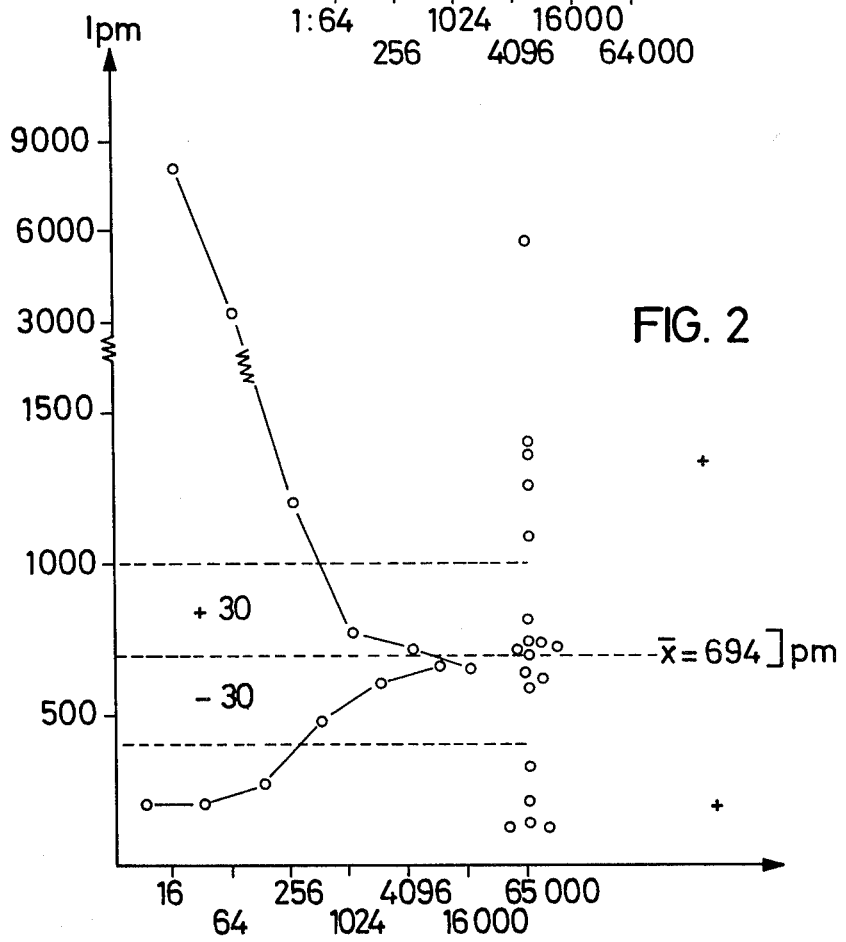

It is preferable to use for the preliminary incubation a quantity of antibody which renders between 10 and 15% of the maximally bindable radioactivity, i.e. within the saturation range of the pertinent standard antibody with a low serum dilution. It has been shown, based upon 3500 preparations with negative controls, that the standard sigma deviation is approximately 10% if the said 10 to 15% antibody binding provides a pulse count of 500 to 1500 per minute. A somewhat higher standard deviation of negative controls (>10%) results from pulse counts of less than 500 per minute. As a certainty threshold, the 3 sigma deviation was chosen, i.e. $HB_s$ antigen is regarded as present if the impulse reduction amounts reproducibly to more than 30% of the negative controls, while $HB_s$ antibody is present if an impulse increase of over 30% is recorded, as this is illustrated in FIG. 2, which is a plot of pulse counts against serum dilution.

Here too an incubation time of 1 hour at 37° C. produced excellent results in the various phases of incubation.

As already outlined above, the assay of the invention yields unequivocally specific results. The difference between the combined assay and the direct antibody radioimmunoassay resides in the fact that the antibody present in the test serum in the latter case is further added to the antibody given in advance. As the $HB_s$ antibody measurement in the combined assay takes place through reduction of the quantity of antibody given in advance, the specificity already described of the $HB_s$ antibody determination is at the same time the basis of the specific $HB_s$ antigen measurement. An unspecific antibody reduction caused by other antibodies can then be excluded. An exception are the antibodies possibly present in the sample material which are directed against the $HB_s$ antibody itself. The performance of the assay is illustrated in FIG. 4, which is a graphic representation of the assay procedure according to the invention.

At least 8 serum samples should be carried along to obtain a reliable mean value at the negative controls.

In the practical application of the combined assay it is indeed an advantage that the reaction can be concluded in 3 full hours (without measuring), but if sufficient time is available, it is advantageous to extend the incubation time by 90 to 120 minutes after addition of the tracer antigen.

It will be understood that the specification and examples are illustrative but not limitative of the present invention and that other embodiments within the spirit and scope of the invention will suggest themselves to those skilled in the art.

What is claimed is:

1. Method of determining the presence of antigen or antibody in an unknown fluid by a solid-phase radioimmunoassay which method comprises incubating a sample of an unknown fluid with a known quantity of an antibody, contacting the mixture obtained with a carrier surface having a coating of known antigen content, again incubating, then aspirating the mixture and washing said carrier surface, adding a pure radioactive tracer antigen, aspirating and washing again, measuring the radioactivity of the coated parts and comparing the radioactive count with the count of a negative control whereby if the count is higher the fluid contains antibody and if the count is lower, the fluid contains antigen.

2. Method as claimed in claim 1 wherein the quantity of antibody employed in the incubation of the unknown sample is 10 to 15% of the maximum antibody quantity bindable by the coating of the carrier surface.

3. Method as claimed in claim 1 wherein the first incubation is carried out for a period from 1 to 16 hours at a temperature of from 20° to 50° C.

4. Method as claimed in claim 3 wherein the incubation is carried out for about one hour at a temperature of about 37° C.

5. Method as claimed in claim 3 wherein the incubation is carried out for a period of about 12 hours at a temperature of about 20° C.

6. Method as claimed in claim 1 wherein micro-titration plates are used as the carrier surface.

7. Method as claimed in claim 6 wherein said microtitration plates are fragmented prior to measuring their radioactivity.

8. Method as claimed in claim 1 wherein said unknown fluid is whole blood.

9. Method as claimed in claim 1 wherein said unknown fluid is plasma.

10. Method as claimed in claim 1 wherein said unknown fluid is urine or saliva.

* * * * *